United States Patent [19]

Gehlhaus et al.

[11] Patent Number: 4,721,734
[45] Date of Patent: * Jan. 26, 1988

[54] PHOTOSENSITIVE HYDROXYLALKYLPHENONES

[75] Inventors: Juergen Gehlhaus, Heppenheim; Manfred Kieser, Darmstadt, both of Fed. Rep. of Germany

[73] Assignee: Merck Patent Gesellschaft mit beschrankter Haftung, Darmstadt, Fed. Rep. of Germany

[*] Notice: The portion of the term of this patent subsequent to Aug. 31, 1999 has been disclaimed.

[21] Appl. No.: 646,285

[22] Filed: Aug. 31, 1984

Related U.S. Application Data

[60] Division of Ser. No. 408,576, Aug. 16, 1972, Pat. No. 4,477,681, which is a continuation-in-part of Ser. No. 99,792, Nov. 26, 1979, Pat. No. 4,347,111, which is a continuation of Ser. No. 906,505, May 16, 1978, abandoned.

[30] Foreign Application Priority Data

May 17, 1977 [DE] Fed. Rep. of Germany ....... 2722264

[51] Int. Cl.$^4$ .......................... C08F 2/50; C08F 4/00; C08F 4/40
[52] U.S. Cl. ........................ 522/8; 430/286; 430/923; 522/12; 522/14; 522/18; 522/20; 522/40; 522/42; 522/43; 522/44; 522/75; 522/182; 522/121
[58] Field of Search ............ 522/42, 33, 34, 36, 522/40, 8; 204/159.23

[56] References Cited

U.S. PATENT DOCUMENTS

| | | |
|---|---|---|
| 2,647,080 | 7/1953 | Joyce ............... 204/159.23 |
| 2,892,865 | 6/1959 | Giraldi et al. . |
| 3,330,659 | 7/1967 | Wainer . |
| 3,660,542 | 5/1972 | Adachi et al. . |
| 3,801,329 | 4/1974 | Sandner et al. . |
| 3,933,682 | 1/1976 | Bean . |
| 3,965,157 | 6/1976 | Harrison . |
| 4,017,652 | 4/1977 | Gruber . |
| 4,054,719 | 10/1977 | Cordes, III . |
| 4,071,424 | 1/1978 | Darf et al. . |
| 4,284,485 | 8/1981 | Berner . |
| 4,308,400 | 12/1981 | Felder et al. . |
| 4,315,807 | 2/1982 | Felder et al. . |
| 4,318,791 | 3/1982 | Felder et al. . |
| 4,321,118 | 3/1982 | Felder et al. . |
| 4,347,111 | 8/1982 | Gehlhaus ............ 204/159.15 |

FOREIGN PATENT DOCUMENTS

| | | |
|---|---|---|
| 2432563 | 2/1975 | Fed. Rep. of Germany . |
| 2343362 | 8/1979 | Fed. Rep. of Germany . |
| 2156486 | 6/1973 | France . |
| 51-01780 | 2/1976 | Japan . |

OTHER PUBLICATIONS

Bull. Soc. Chim., France 1967, 1047–1052.
J. Gen. Chem. (U.S.S.R.), 30, 792–795 (1960).
J. Med. Chem., 7, 178–186 (1964).
J. Amer. Chem. Soc., 75, 5975–5978 (1953).
Biochem., Zeitschrift, 192, 220–228.
Synthesis, 1975, 391–392.
Tetrahedron Letters, 1974, 4319.
Bull. Soc. Chem., France 1970, 3715–3720.
J. Amer. Chem. Soc., 100, 1962 (1978), antedated by priority.

*Primary Examiner*—John C. Bleutge
*Assistant Examiner*—Arthur H. Koeckert
*Attorney, Agent, or Firm*—Millen & White

[57] ABSTRACT

Compounds of the formula

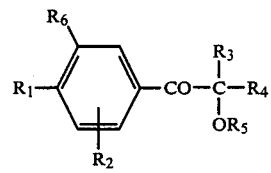

wherein $R_1$ is hydrogen, chlorine, phenyl, dialkylamino of 2–4 carbon atoms or alkyl or alkoxy each of up to 18 carbon atoms; $R_2$ is hydrogen, chlorine, bromine or alkyl or alkoxy each of up to 4 carbon atoms; $R_3$ and $R_4$, which can be the same or different, each is hydrogen or alkyl of up to 6 carbon atoms; $R_5$ is hydrogen or alkyl or alkanoyl each of up to 4 carbon atoms; and $R_6$ is hydrogen or methyl, with the proviso that not all of $R_1$ to $R_6$ simultaneously are hydrogen, are effective photosensitizers, especially for photopolymerization of unsaturated compounds and for hardening of printing dyes.

11 Claims, No Drawings

PHOTOSENSITIVE HYDROXYLALKYLPHENONES

CROSS REFERENCE TO RELATED APPLICATIONS

This is a divisional application of Ser. No. 408,576, filed 8/16/82, now U.S. Pat. No. 4,477,681, which is a continuation-in-part of Ser. No. 099,792, filed 11/26/79, now U.S. Pat. No. 4,347,111, which is a continuation application of Ser. No. 906,505, filed May 16, 1978, now abandoned.

BACKGROUND OF THE INVENTION

Many reactions in organic chemistry are accelerated or in some instances even made possible by irradiation with visible or ultra-violet (UV) radiation. Such reactions include, for example, fission reactions, e.g., in the vitamin D series, rearrangement reactions, e.g., cis-transisomerizations, and addition reactions, e.g., of maleic acid to benzene. However, the technically most important addition reactions of this kind are the photochemically initiated polymerization reactions.

For all of these reactions, it is necessary that at least a portion of the reaction mixture be capable of absorbing irradiated visible or UV radiation. When this portion is one of the reaction components, the reactions can be carried out without further additives simply by appropriate irradiation of the reaction mixture. However, frequently the reaction components are not able to absorb a sufficient amount of the photochemically effective irradiation. In such cases, substances called photosensitizers are frequently added. These do not participate in the reaction but are able to absorb the visible UV irradiation and to transfer the absorbed energy to one of the reaction components. Important criteria for the choice of such sensitizers are, inter alia, the nature of the reaction to be carried out, the relationship of the absorption spectrum of the sensitizer to the spectral energy distribution of the available source of radiation, the solubility of the sensitizer in the reaction mixture and the influence on the end product of residues of the sensitizer and/or the products resulting therefrom during the photochemical reaction.

As sensitizers for the photopolymerization of unsaturated compounds, previously there have principally been used benzophenone derivatives, benzoic ethers, benzil monoacetals and α-haloacetophenone derivatives. However, these substances possess various disadvantages which distinctly limit their industrial usefulness. Such disadvantages include, in particular, the tendency of monomers or prepolymers to polymerize when mixed with photosensitizers of these groups prior to irradiation, i.e., in the dark. Consequently, many reaction mixtures containing such sensitizers possess only a low stability in the dark. Other compounds from these classes possess only a low chemical stability; thus, for example, some benzil monoacetals are split even by very small amounts of water, e.g., by atmospheric humidity, into benzil and alcohol. Furthermore, others of these known sensitizers cause a yellowing of the resultant photopolymerized polymers, which, especially in the case of normally colorless synthetic resins or in particular in the case of UV-hardened printing dyes, is highly undesirable. For this last-mentioned field of use, the generally low solubility of the known sensitizers in the monomers or prepolymers often plays an important role. Since, as a rule, printing dyes contain considerable amounts of colored pigments which absorb a large part of the irradiated energy, which is thus unavailable for photochemical reactions, a comparatively large amount of sensitizer must be added. Frequently, as a result, amounts up to 5 to 10 weight percent of the reaction mixture, i.e., the printing dye, must be employed whereas otherwise in the synthetic resin industry, in the absence of coloring additives, only 1 to 2 weight percent are often completely sufficient. Usually even this relatively low concentration can barely be achieved with the sparingly soluble known sensitizers. In the case of the much higher concentrations necessary in printing dyes, the known sensitizers frequently partially crystallize out. In addition to the fact that the proportions which have crystallized out no longer act sensitizingly, after some time, the resultant crystallites also damage the printing plates consisting of relatively soft materials.

Acetophenone and derivatives thereof have also been suggested and used as photosensitizers, especially for photochemical cyclo-additions. [e.g., K. GOLLNICK "Type II Photooxidation Reactions" in Advances in Photochemistry, Vol. 6, pages 1–122 (Interscience Publishers, New York 1966, Editors: A. N. NOYES, G. S. HAMMOND and J. N. PITTS)]. The results obtained with compounds of this class, especially the quantum yields of the photochemical reactions sensitized therewith, are mostly markedly poorer than, for example, the results obtained with benzophenone.

SUMMARY OF THE INVENTION

Accordingly, it is an object of this invention to provide photosensitizers, especially for the photopolymerization of unsaturated compounds, which, in admixture with the other reaction components, are storage stable in the dark, which themselves and due to products derived from them do not cause yellowing of the reaction products and which possess a solubility which is as high as possible in the monomers or prepolymers normally subjected to a photopolymerization.

It is another object of this invention to provide such photosensitizers which possess the greatest possible photosensitizing effectiveness in the wavelength range of 250 to 500 nm, preferably between 300 and 400 nm.

Upon further study of the specification and appended claims, further objects and advantages of this invention will become apparent to those skilled in the art.

These objects have been attained by providing, in a method aspect, a method of photosensitizing which comprises using compounds of formula (I),

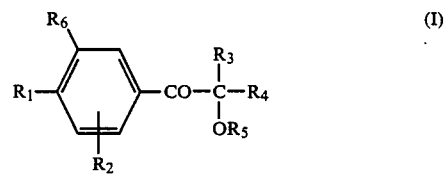

wherein $R_1$ is hydrogen, chlorine, phenyl, dialkylamino of 2–4 carbon atoms or alkyl or alkoxy of, in each case, up to 18 carbon atoms; $R_2$ is hydrogen, chlorine, bromine or alkyl or alkoxy of, in each case, up to 4 carbon atoms; $R_3$ and $R_4$, which can be the same or different, each is hydrogen or alkyl of up to 6 carbon atoms; $R_5$ is hydrogen or alkyl or alkanoyl of, in each case, up to 4 carbon atoms and $R_6$ is hydrogen or methyl; wherein, however, all residues $R_1$ to $R_6$ are not simultaneously hydrogen atoms;

as photosensitizers, especially for photopolymerization of unsaturated compounds, as well as for the UV hardening of photohardenable printing dyes.

In a composition aspect, this invention relates to new compounds of formula (II),

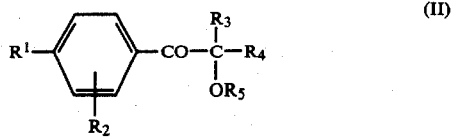

wherein $R_1$ is hydrogen, phenyl, dialkylamino of 2-4 carbon atoms or alkyl or alkoxy of, in each case, up to 18 carbon atoms; $R_2$ is hydrogen, chlorine, bromine or alkyl or alkoxy of, in each case, up to 4 carbon atoms; $R_3$ and $R_4$ are the same or different and each is alkyl of up to 6 carbon atoms or one of $R_3$ and $R_4$ is hydrogen; and $R_5$ is hydrogen or alkyl or alkanoyl of, in each case, up to 4 carbon atoms; with the proviso (a) that $R_1$ and $R_2$ are not simultaneously hydrogen atoms; (b) that $R_1$ is not methyl, methoxy or phenyl when (i) $R_2$ is hydrogen and (ii) $R_3$ and $R_4$ are both methyl or one is hydrogen and the other is methyl; and (c) that $R_2$ is not methyl when (i) $R_1$ is hydrogen and (ii) $R_3$ and $R_4$ are both methyl or one is hydrogen and the other is methyl.

In another composition aspect, this invention relates to compounds of formula (II)

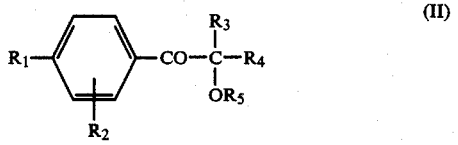

wherein $R_1$ is hydrogen, phenyl, dialkylamino of 2-4 C-atoms or alkyl or alkoxy each of up to 18 C-atoms; $R_2$ is hydrogen, chlorine, bromine or alkyl of up to 4 C-atoms; $R_3$ and $R_4$ are the same or different and each is alkyl of up to 6 C-atoms, and $R_5$ is hydrogen, or alkyl or alkanoyl each up to 4 C-atoms; with the proviso that (a) If $R_1$ and $R_2$ are both hydrogen and $R_3$ and $R_4$ are both methyl: $R_5$ is not hydrogen, methyl or acetyl;
(b) If $R_2$ and $R_5$ are both hydrogen and $R_3$ and $R_4$ are both methyl: $R_1$ is not methyl, methoxy or phenyl;
(c) if $R_2$ is 2-methyl and $R_1$ and $R_5$ are both hydrogen: at least one of $R_3$ and $R_4$ is different from methyl;
(d) if $R_1$, $R_2$ and $R_5$ are hydrogen and $R_4$ is ethyl; $R_3$ is neither methyl nor ethyl.

In a further composition aspect, this invention relates to compounds of formula II

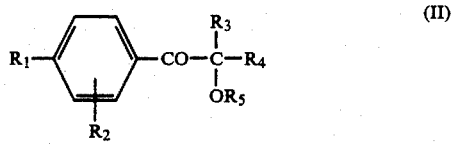

wherein $R_1$ is hydrogen, phenyl, dialkylamino of 2-4 C-atoms or alkyl or alkoxy each of up to 18 C-atoms; $R_2$ is hydrogen, chlorine, bromine or alkyl of up to 4 C-atoms; $R_3$ and $R_4$ are the same or different and each is alkyl of up to 6 C-atoms; and $R_5$ is hydrogen, or alkyl or alkanoyl each up to 4 C-atoms; with the proviso (a) that $R_1$ and $R_2$ are not simultaneously hydrogen atoms; (b) that $R_1$ is not methyl, methoxy or phenyl when (i) $R_2$ is hydrogen and (ii) $R_3$ and $R_4$ are both methyl, or one is hydrogen and the other is methyl; and (c) that $R_2$ is not methyl when (i) $R_1$ is hydrogen and (ii) $R_3$ and $R_4$ are both methyl.

In further method aspect, this invention relates, in a method of photopolymerizing a photopolymerizable composition comprising at least one photopolymerizable unsaturated compound and a photosensitizingly effective amount of at least one photosensitizer, comprising irradiating the photopolymerizable composition with effective radiation, to the improvement wherein the photosensitizer comprises at least one compound of formula (I)

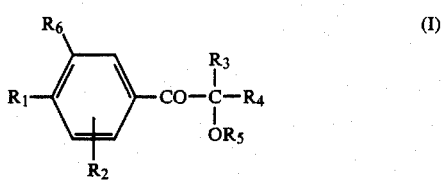

wherein $R_1$ is hydrogen, chlorine, phenyl, dialkylamino of 2-4 C-atoms or alkyl or alkoxy each of up to 18 C-atoms; $R_2$ is hydrogen, chlorine, bromine or alkyl or alkoxy each of up to 4 C-atoms; $R_3$ and $R_4$, which can be the same or different, each is alkyl of up to 6 C-atoms; and $R_5$ is alkyl or alkanoyl each of up to 4 C-atoms and $R_6$ is hydrogen or methyl.

DETAILED DISCUSSION

In view of the common structural characteristics of conventional photosensitizers which, as a rule, contain two possibly substituted phenyl nuclei, the aromatic system of which are cross-conjugated via one or two carbon atoms, it is surprising that the hydroxyalkyl ketones to be used according to this invention, having only one aromatic ring possess such a good photosensitizing action especially in view of the relatively poor results previously obtained with acetophenone derivatives as discussed above.

It has now been found that the compounds of formula (I) possess a good photosensitizing effectiveness for irradiation in the wavelength region of 250–500 nm and are clearly more soluble in the monomers of prepolymers generally employed for photopolymerizations, e.g., based upon unsaturated esters, such as acrylic acid esters, methacrylic acid esters or maleic acid esters, or styrene, than are most of the sensitizers previously employed. Furthermore, the solutions of the photosensitizers of the formula (I) in these monomers and prepolymers generally possess a better storage stability in the dark than, for example, analogous solutions of benzoin ethers. Finally, in photopolymerizations using the sensitizers of formula (I), yellowing of the polymers is not observed or is found to only a substantially smaller degree than for the conventional sensitizers.

In formula (I), $R_1$ is preferably alkyl or alkoxy of up to 18 carbon atoms, preferably 1-12 carbon atoms, a chlorine atom, dialkylamino of 2-4 carbon atoms or phenyl. Especially preferred as $R_1$ are alkyl groups of up to 12 carbon atoms or the dimethylamino group. $R_2$ is most preferably hydrogen. For the other embodiments $R_2$ is preferred in the 3-position. It can also preferably be a chlorine or bromine atom or a methyl or methoxy group in the 2- or 3-position, preferably in the 3-position, of the phenyl nucleus.

For $R_3$ and $R_4$, preferably not more than one is a hydrogen atom. Especially preferred are compounds in which both residues $R_3$ and $R_4$ are alkyl groups which together contain 2 to 10, preferably 2 to 8 carbon atoms.

$R_5$ is preferably hydrogen. When it is alkyl or alkanoyl, of these methyl, ethyl and acetyl are preferred.

Finally, $R_6$ is preferably hydrogen. If is preferably only a methyl group when $R_1$ is hydrogen and $R_2$ is 2-methyl.

Consequently, according to this invention, there are especially employed as photosensitizers those compounds of formula (I) in which at least one of $R_1$ to $R_6$ has one of the above-mentioned preferred meanings. Some groups of compounds to be used preferably according to the invention can be expressed by the following partial formulae (Ia) to (Ip) which correspond to formula (I) and wherein the residues not more precisely defined are defined as for the formula (I) but wherein in (Ia) $R_1$ is alkyl of 1–12 carbon atoms;
in (Ib) $R_1$ is alkyl of 3–12 carbon atoms;
in (Ic) $R_1$ is dimethylamino;
in (Id) $R_2$ is hydrogen;
in (Ie) $R_2$ is 3-chloro-, 3-bromo-, 3-methyl or 3-methoxy;
in (IF) $R_1$ is alkyl of 1–4 carbon atoms and $R_2$ is as defined in (Ie);
in (Ig) $R_3$ and $R_4$ are both methyl;
in (Ih) $R_3$ is ethyl and $R_4$ is n-butyl;
in (Ii) $R_3$ is methyl and $R_4$ is ethyl;
in (Ij) $R_5$ is hydrogen;
in (Ik) $R_5$ is methyl, ethyl or acetyl;
in (Il) $R_1$ is alkyl of 3–12 carbon atoms and $R_2$ and $R_5$ both are hydrogen;
in (Im) $R_1$ is alkyl of 3–12 carbon atoms, $R_2$ is hydrogen and $R_3$ and $R_4$ both are methyl;
in (In) $R_1$ is alkyl of 1–12 carbon atoms, $R_2$ is hydrogen, $R_3$ is ethyl and $R_4$ is n-butyl;
in (Io) $R_6$ is hydrogen;
in (Ip) $R_1$ is hydrogen, $R_2$ is 2-methyl and $R_6$ is methyl.

The foregoing discussion of the entities $R_1$–$R_6$ also applies to formula II where applicable.

The preparation of some of the compounds of formula (I) to be used according to this invention is known from Bull. Soc. Chim. France 1967, 1047–1052; J. Amer. Chem. Soc. 75 (1953), 5975–5978; and Zh. Obshch. Khim. 34 (1964), 24–28, all of which are incorporated by reference herein. However, their outstanding photosensitizing effectiveness is not disclosed in these literature references nor rendered obvious thereby. The new compounds of formula (I) can be prepared analogously to the standard processes of organic chemistry described in the mentioned literature references.

In a preferred preparation process, a benzene derivative of formula (III)

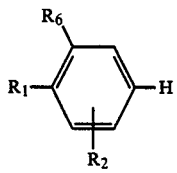
(III)

wherein $R_1$, $R_2$ and $R_6$ are as defined above, is reacted in the presence of a Lewis acid, for example, aluminum chloride, with an α-halocarboxylic acid chloride of formula (IV)

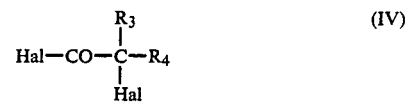
(IV)

wherein $R_3$ and $R_4$ are as defined above and Hal is a halogen atom, preferably chlorine or bromine, and the so obtained α-haloketone of formula (V)

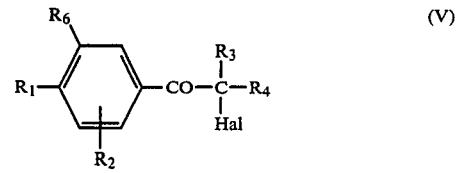
(V)

wherein $R_1$, $R_2$, $R_3$, $R_4$, $R_6$ and Hal are as defined above is conventionally saponified to the hydroxyalkylphenone of the formula (I)($R_5$=H). When $R_3$ and $R_4$ are alkyl, this saponification is conducted by simple heating of the α-haloketone (V) with a concentrated solution of an alkali metal hydroxide in a solvent miscible with water, such as, for example, methanol, ethanol, isopropanol, acetone or dimethyl sulphoxide. If one or both of the residues $R_3$ and $R_4$ are hydrogen, then, as a rule, it is expedient first to convert the α-haloketone (V), by reaction with a carboxylic acid salt, for example, sodium acetate, in an anhydrous organic solvent, into an alkanoyloxyalkylphenone of the formula (I) ($R_5$=alkanoyl). If desired, this is converted by hydrolysis in the presence of a weakly basic compound, for example, sodium hydrogen carbonate, into the hydroxyalkylphenone (I, $R_5$=H).

Alkanoyloxyalkylphenones of formula (I) ($R_5$=alkanoyl) can also be prepared by acylation of the hydroxyalkylphenones (I, $R_5$=H) with suitable carboxylic acid derivatives, for example, carboxylic acid anhydrides or halides.

The alkoxyalkylphenones of formula (I) ($R_5$=alkyl) can be prepared, for example, by reaction of the α-haloketones (V) with an alcoholate, for example, sodium ethylate, in an anhydrous organic solvent, such as, for example, ethanol.

In addition to the Friedel-Crafts reaction of (III) with (IV), the α-haloketones (V) can also be conventionally prepared by halogenation, preferably chlorination or bromination, of a phenone of formula (VI)

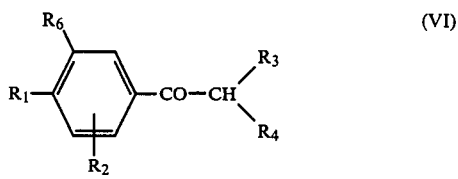
(VI)

wherein $R_1$, $R_2$, $R_3$, $R_4$ and $R_6$ are as defined above. This process is then preferably employed when the phenone (VI) is readily obtainable and no side reactions occur in the halogenation, e.g., halogenation of benzyl carbon atoms in $R_1$, $R_2$ and/or $R_6$.

Furthermore, the hydroxyalkylphenones of formula (I) can be prepared by reacting a Grignard compound of formula (VII)

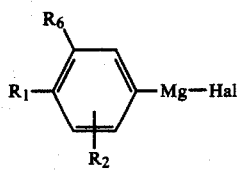

wherein $R_1$, $R_2$, $R_6$ and Hal are as defined above, with a cyanohydrin compound having a protected oxygen atom of formula (VIII)

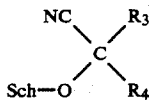

wherein Sch—O— is an hydroxyl group protected against Grignard compounds, for example, a tetrahydropyranyl ether group, and $R_3$ and $R_4$ are as defined above, and subsequently conventionally hydrolyzing the reaction mixture in the presence of an acid. This preparation process is preferred for the synthesis of compounds of formula (I) in which $R_1$ is a dialkylamino group.

The photosensitizers according to this invention are employed in the customary fashion for such products, e.g., by analogy to the use of any of the conventional photosensitizers mentioned herein. For example, for the photopolymerization of unsaturated compounds, 0.05–15 wt.%, preferably 0.1 to 12 wt.%, of one or more compounds of formula (I), optionally together with other conventional photosensitizers is dissolved in the unsaturated monomer, its prepolymer or its precopolymer. These solutions are then irradiated with visible or UV radiation in the wavelength range of 250 to 500 nm, preferably of 300 to 400 nm. Suitable unsaturated compounds which can be photopolymerized using the sensitizers of this invention include all those having C=C double bonds which are activated by, for example, halogen atoms; carbonyl, cyano, carboxy, ester, amide, ether or aryl groups; or by other conjugated double or triple bonds. Examples of such compounds include vinyl chloride, vinylidene chloride, acrylic acid methyl ester, acrylonitrile, hydroxyethyl acrylate, cyclohexyl acrylate, hydroxypropyl acrylate, hydroxyethyl methacrylate, benzyl acrylate, 2-ethylhexyl acrylate, phenyloxyethyl acrylate, lower alkoxyethyl acrylate, tetrahydrofurfuryl acrylate, N-vinylpyrrolidone, N-vinylcarbazole, vinyl acetate, styrene, divinylbenzene and substituted styrenes. Polyunsaturated compounds, such as trimethylolpropane diacrylate, propoxylated bisphenyl-A diacrylate and dimethacrylate and 1,6-hexanediol diacrylate and pentaerythritol triacrylate can also be photopolymerized using the sensitizers of this invention. Suitable prepolymers and and precopolymers include, for example, unsaturated polyesters, acrylic materials, epoxy materials, urethanes, silicones, amine polyamide resins and, in particular, acrylated resins, such as acrylated silicone oil, acrylated polyesters, acrylated urethanes, acrylated polyamides, acrylated soya bean oil, acrylated epoxy resin and acrylated acrylic resin.

The photopolymerizable compounds or mixtures of this invention can be stabilized by the addition of known inhibitors, e.g., hydroquinone, in the conventional amounts, without the sensitizer action of the photosensitizers according to this invention being notably impaired.

Furthermore, they can contain pigments or dyestuffs, such as are conventional in the photochemical hardening of printing dyes. In this case, the amount of sensitizer is chosen to be higher, for example, 6–12 wt.%, whereas for colorless photopolymerizable products, 0.1–3 wt.% is, in most cases, completely sufficient.

Suitable photosensitizers which are known and can optionally be used together with the sensitizers according to this invention include, for example, Michler's ketone, (4,4'-bis-[dimethylamino]-benzophenone), 4,4'-bis-(diethylamino)-benzophenone, p-dimethylaminobenzaldehyde, 4,4'-bis-(dimethylamino)-benzil, p-dimethylaminobenzophenone, p-dimethylaminobenzoic, p-dimethylaminobenzil, N-substituted 9-acridinones, the amino- (or phenyl-) carbonyl compounds described in U.S. Pat. No. 3,661,588, the p-aminophenylcarbonyl compounds described in U.S. Pat. No. 3,552,973, acetophenone, propiophenone, xanthone, benzaldehyde, benzophenone, p-chlorobenzophenone, biacetyl, benzil, fluorenone, 3-nitro-4-chlorobenzophenone-2-carboxylic acid, phenanthrenequinone, benzoin and alkyl ethers of benzoin, 2-chlorothioxanthone, 10-thioxanthenone, 1-phenyl-1,2-propanedione oxime and the esters and ethers thereof, isatin, anthrone, hydroxypropyl benzoate, benzoyl benzoate acrylate, 2,4-dimethylbenzophenone, benzoylbiphenyl, acenaphthenoquinone and dibenzosuberone.

Suitable sources of irradiation for effecting the photopolymerization, include sunlight or artificial radiation. However, there are advantageously also used mercury vapor high or low pressure lamps, xenon and tungsten lamps. Laser light sources can also be employed.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Examples 1 to 6 concern the preparation of compounds of formula (I) to be used according to the invention:

EXAMPLE 1

Into a suspension of 665 g of aluminum chloride in 2000 ml of 1,2-dichloroethane are introduced at 0°, 740 g of α-chloroisobutyryl chloride (prepared by chlorination of isobutyryl chloride in the presence of catalytic amounts of chlorosulphonic acid and chloroanil). To this mixture are added dropwise, with vigorous stirring, at 0° to 5°, 1230 g of commercially available technical dodecylbenzene (Marlican ® of Chemische Werke Huels AG, Marl). After completion of the dropwise addition, the reaction mixture is stirred at this temperature for a further 45 minutes and subsequently stirred into a mixture of 1000 g of ice and 400 ml of concentrated hydrochloric acid. The organic layer is separated off, washed twice with 300 ml amounts of dilute hydrochloric acid, dried over calcium chloride and evaporated. The 1-(4'-dodecylphenyl)-2-chloro-2-methyl-propanone-(1) remaining behind is dissolved in 2000 ml of isopropyl alcohol with stirring and gentle heating. This solution is heated to the boil for 1½ hours, with stirring, with 550 ml of 32% aqueous sodium hydroxide solution and subsequently poured into 2000 ml of water. The aqueous reaction mixture is extracted with 1000 ml of toluene, the extract washed with 1000 ml of 10% aqueous sodium chloride solution, dried over sodium sulphate and evaporated. The 1-(4'-dodecylphenyl)-2-hydroxy-2-methyl-propanone-(1) remaining behind is distilled under reduced pressure; b.p.$_{0.01}$ 180°–183°.

There are prepared analogously:
1-(4'-hexylphenyl)-2-hydroxy-2-methyl-propanone-(1),
1-(4'-octylphenyl)-2-hydroxy-2-methyl-propanone-(1),
1-(4'-nonylphenyl)-2-hydroxy-2-methyl-propanone-(1),
1-(4'-hexadecylphenyl)-2-hydroxy-2-methyl-propanone-(1),
1-(4'-octadecylphenyl)-2-hydroxy-2-methyl-propanone-(1),
1-(4'-hexyloxyphenyl)-2-hydroxy-2-methyl-propanone-(1),
1-(4'-octyloxyphenyl)-2-hydroxy-2-methyl-propanone-(1),
1-(4'-dodecylphenyl)-2-hydroxy-2-ethyl-hexanone-(1),
1-(4'-dodecylphenyl)-2-hydroxy-2-methyl-butanone-(1),
1-(4'-chlorophenyl)-2-hydroxy-2-methyl-propanone-(1), b.p.$_{0.1}$ 117°–118° and
1-phenyl-2-hydroxy-2-methyl-propanone-(1), b.p.$_{0.3}$ 86°–88°.

EXAMPLE 2

Analogously to Example 1, with 133 g of aluminum chloride in 500 ml of dichloroethane, there are prepared from 141 g of α-chloroisobutyryl chloride and 92 g of toluene, 1-(4'-methylphenyl)-2-chloro-2-methyl-propanone-(1) and the crude product dissolved in 500 ml of anhydrous methanol. A solution of 54 g of sodium methylate in 1500 ml of methanol is added dropwise, with stirring, the reaction mixture warmed to 60° and then left to stand for 16 hours. Subsequently, the precipitated sodium chloride is filtered off and the filtrate evaporated. The 1-(4'-methylphenyl)-2-methoxy-2-methylpropanone remaining behind is distilled under reduced pressure; there are obtained 98.4 g with b.p.$_{0.03}$ 75°–77°.

There are prepared analogously:
1-(4'-methylphenyl)-2-ethoxy-2-methyl-propanone-(1),
1-(4'-methylphenyl)-2-butoxy-2-methyl-propanone-(1),
1-(4'-isopropylphenyl)-2-ethoxy-2-methyl-propanone-(1),
1-(4'-pentylphenyl)-2-methoxy-2-methyl-propanone-(1),
1-(4'-methylphenyl)-2-methoxy-2-ethyl-hexanone-(1) and
1-(4'-dodecylphenyl)-2-ethoxy-2-methyl-propanone-(1).

EXAMPLE 3

Analogously to Example 1, with 335 g of aluminum chloride in 1000 ml of dichloroethane, from 300 g of toluene and 455 g of α-chloropropionyl chloride there are prepared 550 g of 1-(4'-methylphenyl)-2-chloropropanone-(1). The crude material is dissolved in 3000 ml of ethanol and heated to the boil for 15 hours with 392 g of anhydrous potassium acetate. Subsequently, the reaction mixture is evaporated under reduced pressure, the residue taken up in 2500 ml of diethyl ether and filtered. The filtrate is evaporated and the 1-(4'-methylphenyl)-2-acetoxy-propanone-(1) remaining behind distilled under reduced pressure; yield: 364 g, b.p.$_{0.3}$ 115°–122°.

There are prepared analogously:
4-tert-butyl-α-acetoxy-acetophenone; b.p.$_{0.3}$ 140°–143°; and
1-(4'-tert-butylphenyl)-2-acetoxy-2-methyl-propanone-(1), b.p.$_{0.3}$ 144°–148°.

EXAMPLE 4

A solution of 371 g of 1-(4'-methylphenyl)-2-acetoxy-propanone-(1) in 3000 ml of isopropyl alcohol is mixed with a solution of 151 g of sodium hydrogen carbonate in 1200 ml of water and the mixture heated to the boil for 15 hours, while stirring. Subsequently, the solvent is distilled off under reduced pressure, the residue taken up in 500 ml of water and extracted three times with 300 ml amounts of diethyl ether. The combined ether extracts are dried over sodium sulphate and evaporated. The 1-(4'-methylphenyl)-2-hydroxypropanone-(1) remaining behind is distilled under reduced pressure; yield: 224 g, b.p.$_{0.3}$ 85°–90°.

There are prepared analogously:
1-(3',4'-dimethylphenyl)-2-hydroxy-2-methyl-propanone-(1), b.p.$_{0.6}$ 88°–90°;
1-(4'-methoxyphenyl)-2-hydroxy-2-methyl-propanone-(1), b.p.$_{0.1}$ 125°–129°;
1-(4'-biphenylyl)-2-hydroxy-2-methyl-propanone-(1), m.p. 85°;
1-(4'-isopropylphenyl)-2-hydroxy-butanone-(1),
1-(4'-isopropylphenyl)-2-hydroxy-propanone-(1),
1-(4'-tert-butylphenyl)-2-hydroxy-propanone-(1) and
1-(4'-nonylphenyl)-2-hydroxy-hexanone-(1).

EXAMPLE 5

To a solution of 0.1 mol of acetone cyanohydrin tetrahydropyranyl ether in 50 ml of anhydrous tetrahydrofuran is added dropwise, in the course of 40 minutes, with stirring, a solution of 0.075 mol of 4-dimethylaminophenyl magnesium bromide in 100 ml of anhydrous tetrahydrofuran and the reaction mixture heated to the boil for a further 1.5 hours. subsequently, 100 ml of 10% aqueous sulphuric acid are added thereto, the mixture again briefly heated to the boil and then adjusted to a pH value of about 10 with 10% aqueous sodium hydroxide solution. The weakly alkaline reaction mixture is shaken out three times with 150 ml amounts of diethyl ether, the combined ether extracts are washed out with 100 ml of water, filtered and dried over sodium sulphate. After distilling off the ether, there remain 12 g of 1-(4'-dimethylaminophenyl)-2-hydroxy-2-methyl-propanone-(1), which are recrystallized from ethanol; m.p. 115°.

There are prepared analogously:
1-(4'-diethylaminophenyl)-2-hydroxy-2-methyl-propanone-(1),
1-(4'-ethoxyphenyl)-2-hydroxy-2-methyl-propanone-(1),
1-(4'-butyloxyphenyl)-2-hydroxy-2-methyl-propanone-(1),
1-(4'-dimethylaminophenyl)-2-hydroxy-2-methyl-butanone-(1) and
1-(4'-dimethylaminophenyl)-2-hydroxy-2-ethyl-butanone-(1).

EXAMPLE 6

(a) To a suspension of 1038 g of anhydrous aluminum chloride in 3000 ml of dichloroethane there are first added dropwise at 6°–10°, with ice cooling, 750 g of isobutyryl chloride and thereafter 900 g of tert-butylbenzene. The reaction mixture is left to stand for a further 1 hour at 6° and then for 15 hours at room temperature. Subsequently, it is slowly stirred into a solution of 600 ml of concentrated hydrochloric acid in 2400 ml of ice water, the organic phase separated off and the aqueous solution washed out once with 600 ml of dichloroethane. The combined organic phases are washed once each with 500 ml of 5% hydrochloric acid and water, dried over calcium chloride and evaporated. The 1-(4'-tert-butylphenyl)-2-methyl-propanone-(1) remaining behind is distilled under reduced pressure; yield: 1085 g, b.p.$_{0.1}$ 98°–102°.

(b) In the course of 1.5 hours, 550 g of chlorine are passed into a solution of 1007 g of 1-(4'-tert-butylphenyl)-2-methyl-propanone-(1) in 3000 ml of methanol in the presence of 2 ml of concentrated hydrochloric acid and 2 g of iodine at 50°, with stirring. Subsequently, the reaction mixture is further stirred for 30 minutes at 50° and the solvent then distilled off. The residue is taken up in 1000 ml of toluene and washed neutral and chlorine-free with aqueous sodium hydrogen carbonate solution and aqueous sodium thiosulphate solution. Subsequently, the toluene is distilled off and the crude 1-(4'-tert-butylphenyl)-2-chloro-2-methyl-propanone-(1) remaining behind dissolved in 2000 ml of isopropyl alcohol. To this solution are added 420 ml of 32% aqueous sodium hydroxide solution and the reaction mixture heated to the boil for 1.5 hours. After cooling, the reaction mixture is shaken out with 1000 ml of toluene, the toluene extract washed with 1000 ml of 10% aqueous sodium chloride solution, dried over calcium chloride and evaporated. The 1-(4'-butylphenyl)-2-hydroxy-2-methyl-propanone-(1) remaining behind is distilled under reduced pressure; yield: 839 g, b.p.$_{0.1}$ 132°–135°.

There are prepared analogously:

1-(4'-methylphenyl)-2-hydroxy-2-methyl-propanone-(1), b.p.$_{0.5}$ 120°–122°;

1-(4'-ethylphenyl)-2-hydroxy-2-methyl-propanone-(1), b.p.$_{0.3}$ 104°–109°;

1-(4'-isopropylphenyl)-2-hydroxy-2-methyl-propanone-(1), b.p.$_{0.4}$ 108°–109°;

1-(3'-chloro-4'-methoxyphenyl)-2-hydroxy-2-methyl-propanone-(1), m.p. 92°–93°;

1-(3'-bromo-4'-methoxyphenyl)-2-hydroxy-2-methyl-propanone-(1), m.p. 104°–106°;

1-(3'-chloro-4'-methylphenyl)-2-hydroxy-2-methyl-propanone-(1), b.p.$_{0.7}$ 130°–135°;

1-(2',5'-dimethylphenyl)-2-hydroxy-2-methyl-propanone-(1);

1-(2',4'-dimethylphenyl)-2-hydroxy-2-methyl-propanone-(1);

1-(4'-methylphenyl)-2-hydroxy-2-ethyl-hexanone-(1), b.p.$_{0.3}$ 155°–158°;

1-(4'-tert-butylphenyl)-2-hydroxy-2-ethyl-hexanone-(1), b.p.$_{0.2}$ 162°–166°;

1-(4'-isopentylphenyl)-2-hydroxy-2-methyl-propanone-(1);

1-(4'-methylphenyl)-2-hydroxy-2-methyl-butanone-(1);

1-(4'-isopropylphenyl)-2-hydroxy-2-methyl-butanone-(1);

1-(4'-tert-butylphenyl)-2-hydroxy-2-methyl-butanone-(1) and 1-(3',4'-dimethylphenyl)-2-hydroxy-2-methyl-butanone-(1).

The following Examples 7–14 concern the use of the photosensitizers according to this invention in the photopolymerization of unsaturated compounds.

EXAMPLE 7

20 g amounts of a commercially available casting resin based on partly polymerized methyl methacrylate and allyl methacrylate (Plexit®MU 51 of the firm Röhm GmbH, Darmstadt) are each mixed with 0.4 g of a sensitizer according to this invention or of a commercially available product. After complete dissolving of the sensitizer and uniform mixing, the samples are stored in the dark at 60° in closed glass vessels. The samples are tested at regular intervals of time for the commencement of gelling. The results summarized in the following Table are a measure of the dark storage stability of photopolymerizable mixtures with the use of various sensitizers.

TABLE B 7

| Experiment No. | Sensitizer | Dark Storage Stability (Days) |
|---|---|---|
| 1 (prior art) | 1,2-diphenyl-2,2-dimethoxy-ethanone-(1) | 4 |
| 2 (prior art) | Benzoin butyl ether | 0.5 |
| 3 | 1-(4'-dodecylphenyl)-2-hydroxy-2-methyl-propanone-(1) | 5 |

The results show that photopolymerizable mixtures with the sensitizer according to the invention (experiment 3) possess a markedly better dark storage stability than the mixtures with the known sensitizers (experiments 1 and 2).

EXAMPLE 8

Analogously to Example 7, there is determined the dark storage stability of photopolymerizable mixtures each of 20 g of a commercially available casting resin based on unsaturated polyesters and styrene (Palatal P 70 of the firm BASF AG, Ludwigshafen) and 0.4 g each of a sensitizer according to the invention and two known sensitizers. The results are summarized in Table B 8.

TABLE B 8

| Experiment No. | Sensitizer | Dark Storage Stability (Days) |
|---|---|---|
| 1 (Prior art) | 1,2-diphenyl-2,2-dimethoxy-ethanone-(1) | 7 |
| 2 (Prior art) | Benzoin butyl ether | 8 |
| 3 | 1-(4'-dodecylphenyl)-2-hydroxy-2-methyl-propanone-(1) | 12 |

The results also show the superior properties of the sensitizers according to the invention.

EXAMPLE 9

50 g amounts of a commercially available casting resin based on partly polymerized methyl methacrylate and allyl methacrylate (Plexit®MU 51 of the firm Röhm GmbH, Darmstadt) are each mixed with 1.25 g of 1-(4'-tert-butyl-phenyl)-2-hydroxy-2-methyl-propanone-(1) or benzoin butyl ether as sensitizer and coated onto glass plates in 250 μm thicknesses. Immediately after the coating, the layers are irradiated for 30 seconds with a mercury vapor lamp at a distance of 11 cm. From both materials there is formed a hard layer having a non-sticky surface which, for the sensitiver according to this invention is colorless and clear, whereas for the known benzoin ether possesses a markedly yellowish coloration.

EXAMPLE 10

A solution of 0.2 g of 1-(4'-methylphenyl)-2-hydroxy-2-methyl-propanone-(1) in 10 g of trimethylolpropane triacrylate is coated onto a glass plate in a 50 μm thick layer and irradiated as in Example 9. A hard, colorless, glass-clear and highly glossly coating is obtained.

EXAMPLE 11

A solution of 0.1 g of 1-(2',5'-dimethylphenyl)-2-methoxy-2-methylpropanone-(1) and 0.1 g of benzoin butyl ether in 10 g of trimethylol-propane triacrylate is applied with a rubber roller in about 100 μm thickness to white drawing paper. After irradiation as in Example 9, there results a colorless, glossy coating.

EXAMPLE 12

In a solution of 0.8 g of 1-(4'-tert-butylphenyl)-2-hydroxy-2-methylpropanone-(1) and 0.8 g of 1-(4'-isopropylphenyl)-2-hydroxy-2-methylpropanone-(1) in 16.4 g of pentaerythritol triacrylate are dispersed 2.0 g of blue copper phthalocyanin pigment. A rastered stereotype plate is colored with this dispersion and white paper printed therewith. The print surface, which is sticky after the printing process, is subsequently irradiated for 20 seconds at a distance of 11 cm with a mercury vapor lamp. A non-sticky, wipe-proof print is obtained.

EXAMPLE 13

A solution of 0.2 g of 1-phenyl-2-hydroxy-2-methyl-propanone-(1) in 10 g of trimethylol-propane triacrylate is applied with a 25 μm spiral doctor to white glazed paper, and the coating is irradiated as in Example 9. A glossy, colorless non-sticky coating is obtained.

EXAMPLE 14

A solution of 0.75 g of 1-(4'-chlorophenyl)-2-hydroxy-2-methyl-propanone-(1) in a mixture of 20 g of trimethylolpropane triacrylate and 10 g of butanediol diacrylate is applied with a 25 μm spiral doctor to white glazed paper, and the coating is irradiated as in Example 9. A colorless, highly glossy coating is obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a method of photopolymerizing a photopolymerizable composition comprising at least one photopolymerizable unsaturated compound and a photosensitizingly effective amount of at least one photosensitizer, comprising irradiating the photopolymerizable composition with effective radiation, the improvement wherein the photosensitizer comprises at least one compound of the formula

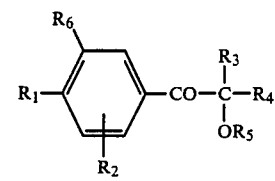

wherein $R_1$ is hydrogen, chlorine, phenyl, dialkylamino of 2-4 C-atoms or alkyl or alkoxy each of up to 18 C-atoms; $R_2$ is hydrogen, chlorine, bromine or alkyl or alkoxy each of up to 4 C-atoms; $R_3$ and $R_4$ which can be the same or different, each is alkyl of up to 6 C-atoms; and $R_5$ is alkyl or alkanoyl each of up to 4 C-atoms and $R_6$ is hydrogen or methyl.

2. The method of claim 1 wherein the photopolymerizable composition is a printing dye.

3. The method of claim 1 wherein the photopolymerizable composition additionally comprises at least one photosensitizer different from that recited in claim 1.

4. The method of claim 2 wherein said composition additionally comprises at least one photosensitizer different from that recited in claim 1.

5. A method of claim 1, wherein $R_5$ is alkanoyl.

6. A method of claim 1, wherein $R_5$ is alkyl.

7. A photopolymerizable composition comprising at least one photopolymerizable unsaturated compound and a photosensitizingly effective amount of at least one compound of the formula

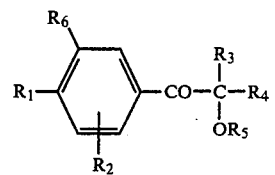

wherein $R_1$ is hydrogen, chlorine, phenyl, dialkylamino of 2-4 C-atoms or alkyl or alkoxy each of up to 18 C-atoms; $R_2$ is hydrogen, chlorine, bromine or alkyl or alkoxy each of up to 4 C-atoms; $R_3$ and $R_4$ which can be the same or different, each is alkyl of up to 6 C-atoms; and $R_5$ is alkyl or alkanoyl each of up to 4 C-atoms and $R_6$ is hydrogen or methyl.

8. A photopolymerizable composition of claim 7 which is a printing dye.

9. The photopolymerizable composition of claim 7 wherein the amount of compound of said formula is 0.05-15 wt.%.

10. A composition of claim 7, wherein $R_5$ is alkanoyl.

11. A composition of claim 7, wherein $R_5$ is alkyl.

* * * * *